US010287532B2

(12) United States Patent
Krubasik et al.

(10) Patent No.: US 10,287,532 B2
(45) Date of Patent: May 14, 2019

(54) DETERGENT COMPOSITION

(75) Inventors: Lucia Krubasik, Ludwigshafen (DE); Judith Preuschen, Ludwigshafen (DE); Andrea Stein, Ludwigshafen (DE); Pavlinka Roy, Ludwigshafen (DE)

(73) Assignee: RECKITT BENCKISER FINISH B.V., hoofddorp (NL)

( * ) Notice: Subject to any disclaimer, the term of this patent is extended or adjusted under 35 U.S.C. 154(b) by 1040 days.

(21) Appl. No.: 13/500,338

(22) PCT Filed: Oct. 6, 2010

(86) PCT No.: PCT/GB2010/051670
§ 371 (c)(1),
(2), (4) Date: May 15, 2012

(87) PCT Pub. No.: WO2011/042737
PCT Pub. Date: Apr. 14, 2011

(65) Prior Publication Data
US 2012/0234359 A1     Sep. 20, 2012

(30) Foreign Application Priority Data
Oct. 9, 2009 (GB) .................................. 0917740.3

(51) Int. Cl.
*C11D 1/722* (2006.01)
(52) U.S. Cl.
CPC .................. *C11D 1/722* (2013.01)
(58) Field of Classification Search
None
See application file for complete search history.

(56) References Cited

U.S. PATENT DOCUMENTS

| | | | |
|---|---|---|---|
| 3,969,134 A * | 7/1976 | Batka ................. A47L 15/4418 |
| | | | 134/26 |
| 4,207,421 A | 6/1980 | Grosser | |
| 6,057,284 A | 5/2000 | Baur et al. | |
| 7,012,052 B1 * | 3/2006 | Kluesener et al. ............ 510/221 |
| 2003/0134765 A1 * | 7/2003 | Kapur ..................... C11D 3/06 |
| | | | 510/220 |
| 2004/0167051 A1 * | 8/2004 | Kessler .................. C11D 1/722 |
| | | | 510/220 |
| 2006/0217286 A1 | 9/2006 | Geoffrey et al. | |
| 2008/0021167 A1 | 1/2008 | Rodrigues | |
| 2008/0113893 A1 * | 5/2008 | Rowland et al. ............. 510/224 |

FOREIGN PATENT DOCUMENTS

| | | |
|---|---|---|
| CA | 1112534 A1 | 11/1981 |
| EP | 0034194 A1 | 8/1981 |
| GB | 2175911 A | 12/1986 |
| JP | 06033100 A | 2/1994 |
| JP | 06080998 A | 3/1994 |
| JP | 08073890 A | 3/1996 |
| JP | 2001131582 A | 5/2001 |
| JP | 2006290942 A | 10/2006 |
| JP | 2008127490 A | 6/2008 |
| WO | 0206438 A1 | 1/2002 |
| WO | 03042347 A1 | 5/2003 |
| WO | 03089563 A2 | 10/2003 |
| WO | 2009033972 A1 | 3/2009 |
| WO | 2010072029 A1 | 7/2010 |

OTHER PUBLICATIONS

English Language Abstract for EP0034194 taken from worldwide.espacenet.com.
International Search Report for PCT/GB2010/051670 dated Jan. 20, 2011.

* cited by examiner

*Primary Examiner* — Nicole Blan
(74) *Attorney, Agent, or Firm* — Troutman Sanders LLP; Ryan Schneider; Chris Davis

(57) ABSTRACT

A liquid hard surface detergent composition comprising a liquid mixed alkoxylate fatty alcohol non-ionic surfactant comprising a greater number of the lower higher alkoxylate group than the higher alkoxylate group in the molecule and a builder. The compositions provide good shine/anti-spotting characteristics on hard surfaces and are especially suitable for use as automatic dishwashing compositions.

23 Claims, No Drawings

DETERGENT COMPOSITION

This is an application filed under 35 USC 371 of PCT/GB2010/051670.

TECHNICAL FIELD

The present invention relates to hard surface detergent compositions such as dishwashing detergent compositions, in particular automatic dishwashing compositions. It also relates to a process of preparing these compositions. In particular the present invention relates to such compositions comprising particular types of non-ionic surfactants and which demonstrate good anti-spotting/shine properties on articles cleansed therewith.

BACKGROUND OF THE INVENTION

It is well known to use detergent compositions in the cleansing of hard surfaces such as cleaning falls and walls and in dishwashing such as automatic dishwashing.

However it is well known that washing hard surfaces with detergent compositions can lead to the cleansed items suffering from spotting due to mineral deposits being left behind once the cleansing operation has been completed. These mineral deposits can be seen as spots on the items and also reduce the shine of the item which has been treated. In dishwashing operations, as well as other cleaning operations the appearance of a shiny surface is tremendously important to consumers as it is perceived as showing thorough and hygienic cleaning results.

The shine of a hard surface is determined mainly by the builder, the polymer and the surfactant system used in the detergent used to clean the surface in question. Typically such detergent compositions are formulated to contain a builder. Builder such as the phosphate builders can bind calcium and magnesium ions, act as alkalinity source for the detergent and are used to buffer the wash liquor in a dishwasher at pH 9 and above sometimes together with other chemicals such as disilicate, metasilicates and soda. Phosphates are also able to disperse existing calcium carbonate in the wash liquor to prevent spotting on glasses as for the aforementioned reasons this is seen as undesirable by the consumer. Thus, phosphates in a detergent have at least four different functions in an alkaline detergent; (1) Providing alkalinity; (2) buffering capacity, (3) complexing of magnesium and calcium ions; and (4) dispersing capacity of calcium carbonate. However, often the use of builders alone is not sufficient to prevent the appearance of spotting on hard surfaces.

Accordingly there is a need in the art to provide detergent compositions for hard surfaces such as kitchenware, walls and floors, which show good anti-spotting properties and which retain the shine on the surface of the item being cleansed. This is especially important for items such as glassware cleaned in a dishwashing operation such as in an automatic dishwashing machine.

It is an object of the present invention to address one or more of the above-mentioned problems.

In particular, it is an object of the present invention to provide detergent compositions for hard surfaces, and in particular and (automatic) dishwashing detergent compositions which provide effective shine/anti-spotting properties on the surfaces it is used to cleanse.

STATEMENT OF INVENTION

It has surprisingly been found that one or more of the above problems are addressed by the compositions of the present invention.

Thus according to a first aspect of the present invention there is provided a liquid hard surface detergent composition comprising a) a liquid mixed alkoxylate fatty alcohol non-ionic surfactant comprising a greater number of moles of the lower higher alkoxylate group than of the higher alkoxylate group in the molecule and b) a builder.

Preferably the composition is an automatic dishwashing detergent composition.

It is preferred that the detergent composition is a gel.

Preferably the mixed alkoxylate fatty alcohol non-ionic surfactant comprises at least two of EO, PO or BO groups and most preferably only EO and PO groups.

The mixed alkoxylate fatty alcohol non-ionic surfactant preferably has a mole ratio of the lower alkoxylate group to the higher alkoxylate group is at least 1.1:1, most preferably of at least 1.8:1, especially at least 2:1. It is also preferred that the mixed alkoxylate fatty alcohol non-ionic surfactant comprises between 3 to 5 moles of the higher alkoxylate group and between 6 to 10 moles of the higher lower group, preferably 4 or 5 moles of PO and 7 or 8 moles of EO and most preferably 4 moles of PO and 8 moles of EO.

Preferably the mixed alkoxylate fatty alcohol non-ionic surfactant has 12-18 carbon atoms.

The detergent preferably comprises 2 to 30% wt of the mixed alkoxylate fatty alcohol non-ionic surfactant.

It is preferred that the detergent composition further comprises a builder, preferably one selected from the phosphate-containing builders, polycarboxylic acids and their salts and amino acid based builders and most preferably from tripolyphosphates, citrates, MGDA and GLDA and salts or derivatives and mixtures thereof.

The detergent composition of the invention preferably further comprises a polymer, especially a sulphonated polymer and most especially a sulphonated polymer comprising monomers of a carboxylic acid or a salt thereof and a sulphonated monomer, especially acrylic acid and/or 2-acrylamido-2-methyl-1-propanesulphonic acid (AMPS).

It is most preferred that the compositions of the present invention comprise additional non-ionic surfactant to the claimed mixed alkoxylate fatty alcohol non-ionic surfactant.

According to a second aspect of the present invention there is provided a method of preparing a detergent composition according to any one of the preceding claims, wherein the detergent composition is prepared at a temperature in the range of from 25-80° C., preferably at a temperature in the range of from 25-60° C. such as 30-50° C.

According to a third aspect the present invention provides a unit dose detergent composition comprising a liquid hard surface detergent composition according to the first aspect of the invention, which composition is enveloped in a water soluble or water dispersible package. The water soluble or water dispersible package preferably has a plurality of compartments. The water soluble or water dispersible package comprises polymeric packaging material which is preferably selected from polyvinyl alcohol, celluloses and cellulose derivatives, starches, gelatine, polyglycolides, gelatine and polylactides copolymers or a mixture or copolymer thereof.

According to a fourth aspect of the invention there is provided a method of reducing spotting on a hard surface by contacting a hard surface with a composition according to the first aspect of the invention or a unit dose composition according to the third aspect of the invention. It is preferred that the method is carried out in an automatic dishwashing machine.

Surprisingly, it has been found that the detergent compositions according to the present invention exhibit good anti-spotting and shine properties upon hard surfaces, especially in dishwashing applications such as in automatic dishwashers.

Unless stated otherwise, all amounts herein are given as the percentage by weight of active ingredient based upon the weight of the total composition.

The term 'substantially free of' as used herein means less than 0.5% wt of the material in question based on the total weight of that material in the detergent composition.

By the term 'water soluble or water dispersible packaging' as used herein is meant a package which at least partially dissolves in water or disperses in water at 20° C. within 10 minutes to allow for egress of the contents of the package into the surrounding water.

By the term 'higher alkoxylate' it is meant the alkoxylate group having the greatest number of carbon atoms in that alkoxylate group. By the term 'lower alkoxylate' it is meant the alkoxylate group having the lowest number of carbon atoms in that alkoxylate group. Thus for a mixed alkoxylate fatty alcohol comprising ethoxylate (EO) and propoxylate (PO) groups the EO is the lower alkoxylate and the PO is the higher alkoxylate. Thus the detergent compositions of the invention comprise mixed alkoxylate fatty alcohols comprising a greater number of EO groups than PO groups. The same applies to other mixed alkoxylates such as those containing EO and butoxylate (BO) or even PO and BO groups.

By the term 'liquid surfactant' as used herein is meant a surfactant which is liquid at 21° C.

A 'liquid composition' as used herein refers coherent composition which shows a tendency to flow as a coherent mass. It includes liquids, gels and pastes. For the avoidance of doubt it does not include solid bodies, granules or powders.

DETAILED DESCRIPTION

The present invention will now be described in further detail.

a) Detergent Composition Format

The composition of the invention may be type of hard surface detergent compositions such as a floor or wall cleaning composition. However it is preferred that the composition of the invention is a dishwashing composition and in particular an automatic dishwashing composition.

The detergent compositions of the present invention are in liquid form as herein defined. According to a preferred aspect of the present invention the dishwashing composition is a gel.

Preferably the detergent compositions of the invention are alkaline, more preferably having a pH in the range of 9-12 as a 1% wt solution at 20° C., most preferably 9.5-11.5. However in some applications it is possible to use less alkaline detergents e.g. those with a pH in the range of from 6.5 to 9, especially from 7 to 8.5 as a 1% wt solution at 20° C.

The detergent compositions of the present invention may be made by any suitable method as well known to the person skilled in the art. However, it is preferred that when the detergent composition is according to the second aspect of the invention.

b) Liquid Mixed Alkoxylate Fatty Alcohol Nonionic Surfactant

Non-ionic surfactants are preferred for automatic dishwashing and some other hard surface cleaning operations as they are considered to be low foaming surfactants.

The standard non-ionic surfactant structure is based on a fatty alcohol with a carbon $C_8$ to $C_{20}$ chain, wherein the fatty alcohol has been ethoxylated or propoxylated. The degree of ethoxylation is described by the number of ethylene oxide units (EO), and the degree of propoxylation is described by the number of propylene oxide units (PO). Surfactants may also comprise butylene oxide units (BO) as a result of butoxylation of the fatty alcohol. Preferably, this will be a mix with PO and EO units. The surfactant chain can be terminated with a butyl (Bu) moiety.

The length of the fatty alcohol and the degree of ethoxylation/propoxylation determines if the surfactant structure has a melting point below room temperature or in other words if is a liquid or a solid at room temperature. It is believed that the mixed alkoxylate fatty alcohol non-ionic surfactant of the present invention provide their advantages for spotting inhibition and shine at least partly because they are liquid at room temperature.

It is preferred that the mixed alkoxylate fatty alcohol nonionic surfactant have a fast wetting properties on glass, plastic and metal surfaces such that at least 90% of the surface is wetted in less than 30 seconds.

The compositions of the invention comprise a liquid mixed alkoxylate fatty alcohol non-ionic surfactant comprising a greater number of moles of the lower higher alkoxylate group than of the higher alkoxylate group in the molecule.

It is especially preferred that the mixed alkoxylate fatty alcohol nonionic surfactant comprises at least two of EO, PO or BO groups and especially a mixture of EO and PO groups, preferably EO and PO groups only.

It is most preferred that the mole ratio of the lower alkoxylate group to the higher alkoxylate group is at least 1.1:1, more preferably at least 1.5:1, and most preferably at least 1.8:1, such as at least 2:1 or even at least 3:1.

An especially preferred mixed alkoxylate fatty alcohol nonionic surfactant according to the present invention comprises between 3 to 5 moles of the higher alkoxylate group and between 6 to 10 moles the higher lower group. Especially preferred are mixed alkoxylate fatty alcohol nonionic surfactants having 4 or 5 moles of the higher alkoxylate group and 7 or 8 moles of the lower alkoxylate group. According to one aspect of the invention a mixed alkoxylate fatty alcohol nonionic surfactant having 4 or 5 PO moles and 7 or 8 EO moles is especially preferred and good results have been obtained with for surfactants with 4 PO moles and 8 EO moles. In an especially preferred embodiment the mixed alkoxylate fatty alcohol non-ionic surfactant is C12-15 8EO/4PO.

Surfactants of the above type which are ethoxylated monohydroxy alkanols or alkylphenols which additionally comprise poly-oxyethylene-polyoxypropylene block copolymer units may be used. The alcohol or alkylphenol portion of such surfactants constitutes more than 30%, preferably more than 50%, more preferably more than 70% by weight of the overall molecular weight of the non-ionic surfactant.

The mixed alkoxylate fatty alcohol non-ionic surfactants used in the compositions of the invention may be prepared by the reaction of suitable monohydroxy alkanols or alkylphenols with 6 to 20 carbon atoms. Preferably the surfactants have at least 8 moles, particularly preferred at least 10 moles of alkylene oxide per mole of alcohol or alkylphenol.

Particularly preferred liquid mixed alkoxylate fatty alcohol non-ionic surfactants are those from a linear chain fatty alcohol with 12-18 carbon atoms, preferably 12 to 15 carbon atoms and at least 10 moles, particularly preferred at least 12 moles of alkylene oxide per mole of alcohol.

When PO units are used they preferably constitute up to 25% by weight, preferably up to 20% by weight and still more preferably up to 15% by weight of the overall molecular weight of the non-ionic surfactant.

Suitable liquid mixed alkoxylate fatty alcohol non-ionic surfactants can be found in the class of reverse block copolymers of polyoxyethylene and poly-oxypropylene and block copolymers of polyoxyethylene and polyoxypropylene initiated with trimethylolpropane.

Suitable types can also be described by the formula:

$R_1O[CH_2CH(CH_3)O]_x[CH_2CH_2O]_y[CH_2CH(OH)R_2]$ where R1 represents a linear or branched chain aliphatic hydrocarbon group with 4-18 carbon atoms or mixtures thereof, R2 represents a linear or branched chain aliphatic hydrocarbon rest with 2-26 carbon atoms or mixtures thereof, x is a value between 0.5 and 1.5 and y is a value of at least 15.

Another group of suitable liquid mixed alkoxylate fatty alcohol non-ionic surfactants can be found in the end-capped polyoxyalkylated non-ionics of formula:

$R_1O[CH_2CH(R_3)O]_x[CH_2]_kCH(OH)[CH_2]_jOR_2$ where $R_1$ and $R_2$ represent linear or branched chain, saturated or unsaturated, aliphatic or aromatic hydrocarbon groups with 1-30 carbon atoms, $R_3$ represents a hydrogen atom or a methyl, ethyl, n-propyl, iso-propyl, n-butyl, 2-butyl or 2-methyl-2-butyl group, x is a value between 1 and 30 and, k and j are values between 1 and 12, preferably between 1 and 5 with the proviso that the molecule contains more of the lower alkoxylate than of the higher alkoxylate. When the value of x is >2 each $R_3$ in the formula above can be different. $R_1$ and $R_2$ are preferably linear or branched chain, saturated or unsaturated, aliphatic or aromatic hydrocarbon groups with 6-22 carbon atoms, where group with 8 to 18 carbon atoms are particularly preferred. For the group $R_3$=H, methyl or ethyl are particularly preferred. Particularly preferred values for x are comprised between 1 and 20, preferably between 6 and 15.

As described above, in case x>2, each $R_3$ in the formula can be different. For instance, when x=3, the group $R_3$ could be chosen to build ethylene oxide ($R_3$=H) or propylene oxide ($R_3$=methyl) units which can be used in every single order for instance (PO)(EO)(EO), (EO)(PO)(EO), (EO)(EO)(PO), (PO)(EO)(PO) and (PO)(PO)(EO). Only the mixed alkoxylates having comprising more of the lower alkoxylate than of the higher alkoxylate are suitable as the claimed mixed alkoxylate fatty alcohol nonionic surfactant. The value 3 for x is only an example and bigger values can be chosen whereby a higher number of variations of (EO) or (PO) units would arise.

Particularly preferred end-capped polyoxyalkylated alcohols of the above formula are those where k=1 and j=1 originating molecules of simplified formula:

$R_1O[CH_2CH(R_3)O]_xCH_2CH(OH)CH_2OR_2$

Other suitable surfactants are disclosed in WO 95/01416, to the contents of which express reference is hereby made.

In a particularly preferred embodiment of the present invention the mixed alkoxylate fatty alcohol non-ionic surfactants have the general formula;

$R_1\text{-}[EO]_n\text{-}[PO]_m\text{-}[BO]_p\text{-}Bu_q$ wherein:
$R_1$ is an alkyl group of between $C_8$ and $C_{20}$;
EO is ethylene oxide;
PO is propylene oxide;
BO is butylene oxide;
Bu is butylene
n and m are integers from 1 to 15;
p is an integer from 0 to 15; and
q is 0 or 1.

Examples of especially preferred mixed alkoxylate fatty alcohol non-ionic surfactants can be found in the Plurafac™, Lutensol™ and Pluronic™ ranges from BASF and the Genapol™ series from Clariant.

The claimed mixed alkoxylate fatty alcohol non-ionic surfactants, and especially the C12-15 fatty alcohol 8EO, 4PO surfactant (commercially available as Genapol EP 2584 ex Clariant, Germany) exhibit;

Excellent wetting of plastic, glass, ceramic and stainless steel

Excellent temperature stability up to 90° C. for processing

Good compatibility with thickeners typically used in the liquid detergent compositions (e.g. PEG)

Stability in alkaline conditions.

The use of a mixture of any of the aforementioned non-ionic surfactants is suitable in compositions of the present invention, e.g. mixtures of alkoxylated alcohols and hydroxy group containing alkoxylated alcohols, provided that they are liquid and have a greater number of moles of the lower higher alkoxylate group than of the higher alkoxylate group in the molecule.

It is preferred that the liquid detergent compositions of the invention comprise 2-30% wt of the liquid mixed alkoxylate fatty alcohol nonionic surfactant more preferably 3-25% wt such as 5-20% wt. If the composition of the invention are present as part of a multi-phase unit dose composition then preferably the claimed non-ionic surfactants are present an amount of from 0.1% wt to 15% wt, more preferably 0.5% wt to 10% wt, such as 0.5 to 7.5% wt based on the total unit dose composition.

Without wishing to be bound by theory it is believed that the film of the surfactant molecules covering the surface of the tableware and the dishwasher prevents the deposition of calcium carbonate on the surfaces and so aids the reduction in spotting and improves the shine of the surfaces being treated. A second and unexpected beneficial effect is an increased "carry over" of surfactant from the main washing cycle into the rinse cycle in the automatic dishwashing machine due to the high concentration of surfactant. This is important for multi-benefit detergents, because they are used without adding extra rinse aid into the reservoir provided in the dishwasher.

Many technological processes require control of liquid spreading over solid surfaces. When a drop is placed on a surface, it can completely wet, partially wet, or not wet the surface. Wetting can be defined in terms of the contact angle ° of a liquid droplet on a particular surface, with a smaller contact angle signifying greater wetting; a contact angle of between 0° and 90° is defined as highly wettable, with 0° being defined as totally wettable.

By reducing the surface tension with the claimed surfactants non-wetting material for water can be made to become partially or completely wetting. Surfactants are absorbed onto the liquid-vapor, solid-liquid, and solid-vapor interfaces, which modify the wetting behavior of hydrophobic materials to reduce the free energy. When surfactants are absorbed onto a hydrophobic surface, the polar head groups face into the solution with the tail pointing outward. In more hydrophobic surfaces, surfactants may form a bilayer on the solid, causing it to become more hydrophilic. As the surfactants are absorbed, the solid-vapor surface tension increases and the edges of the drop become hydrophilic. As a result, the drop spreads and the appearance of spotting is reduced.

This process is time dependent, and the dynamic drop radius can be characterized as the drop begins to spread. The contact angle changes are based on the following equation:

$$\cos \theta(t) = \cos \theta_0 + (\cos \theta_\infty - \cos \theta_0)(1 - e^{-t/\tau})$$

$\Theta_0$ is the initial contact angle
$\Theta_\infty$ is the final contact angle
$\tau$ is the surfactant transfer time scale The wetting properties of a surfactant are therefore key to its performance in detergent compositions used on hard surfaces, such as dishwashing compositions as they regulating the amount of spots left on surfaces as a result of drying of unevenly spread water droplets.

c) Builders

The compositions of the invention comprise a builder. A builder may also be included in any additional detergent composition used in a multi-phase unit dose composition with the composition of the invention. The detergent compositions May comprise conventional amounts of detergent builders which may be either phosphorous based or non-phosphorous based, or a combination of both types. Suitable builders are well known in the art.

If phosphorous containing builders are to be used then it is preferred that mono-phosphates, di-phosphates, tripolyphosphates, polyphosphonates or oligomeric-poylphosphates are used. The alkali metal salts of these agents are preferred, in particular the sodium salts. An especially preferred phosphorous containing builder is sodium tripolyphosphate (STPP). Conventional amounts of the phosphorous-containing builders may be used in the solid detergent compositions, typically in the range of from 15% wt to 80% wt, such as 20% wt to 75% wt, more preferably 25% wt to 60% wt.

The non-phosphorous containing builder may be organic molecules with carboxylic group(s), amino acid based compounds, a succinate based compound or a mixture thereof. The term 'succinate based compound' and 'succinic acid based compound' are used interchangeably herein and these compounds are further described below.

Builder compounds which are organic molecules selected from water-soluble monomeric polycarboxylic acids and/or their acid forms may be used according to the invention. Suitable polycarboxylic acids include acyclic, alicyclic, heterocyclic and aromatic carboxylic acids. Suitable examples of such compounds include citric acid, fumaric acid, tartaric acid, maleic acid, lactic acid, (ethylenedioxy)diacetic acid, tartronic acid, lactic acid, glycolic acid, malonic acid, diglycolic acid and fumaric acid and salts and derivatives thereof, especially the water soluble salts thereof. Preferred salts of the abovementioned compounds are the ammonium and/or alkali or alkaline earth metal salts, e.g. the ammonium, lithium, sodium, potassium or calcium salts, and particularly preferred salts are the sodium salts. These acids may be used in their monomeric or oligomeric form. An especially preferred builder is sodium citrate.

Preferred examples of amino acid based compounds according to the invention are MGDA (methyl-glycine-diacetic acid, and salts and derivatives thereof) and GLDA (glutamic-N,N-diacetic acid) and salts and derivatives thereof. Other suitable builders are described in U.S. Pat. No. 6,426,229 which is incorporated by reference herein. A preferred MGDA compound is a salt of methyl glycine diacetic acid. Suitable salts include the triammonium salt, the tripotassium salt and, preferably, the trisodium salt. A preferred GLDA compound is a salt of glutamic diacetic acid. Suitable salts include the tetraammonium salt, the tetrapotassium salt and, preferably, the tetrasodium salt. Especially preferred are the sodium salts thereof.

In particular suitable builders include; for example, aspartic acid-N-monoacetic acid (ASMA), aspartic acid-N,N-diacetic acid (ASDA), iminodisuccinic acid (IDA), aspartic acid-N-monopropionic acid (ASMP), N-(2-sulfomethyl) aspartic acid (SMAS), N-(2-sulfoethyl)aspartic acid (SEAS), N-(2-sulfomethyl)glutamic acid (SMGL), N-(2-sulfoethyl)glutamic acid (SEGL), N-methyliminodiacetic acid (MIDA), α-alanine-N,N-diacetic acid (α-ALDA), β-alanine-N,N-diacetic acid (β-ALDA), serine-N,N-diacetic acid (SEDA), isoserine-N,N-diacetic acid (ISDA), phenyl-alanine-N,N-diacetic acid (PHDA), anthranilic acid-N,N-diacetic acid (ANDA), sulphanilic acid-N,N-diacetic acid (SLDA), taurine-N,N-diacetic acid (TUDA) and sulphomethyl-N,N-diacetic acid (SMDA) and alkali metal salts or ammonium salts thereof.

Preferred succinate compounds are described in U.S. Pat. No. 5,977,053 and have the formula;

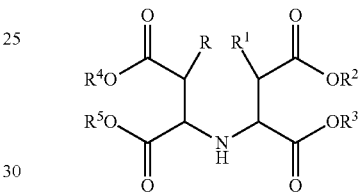

in which R, $R^1$, independently of one another, denote H or OH, $R^2$, $R^3$, $R^4$, $R^5$, independently of one another, denote a cation, hydrogen, alkali metal ions and ammonium ions, ammonium ions having the general formula $R^6R^7R^8R^9N+$ and $R^6$, $R^7$, $R^8$, $R^9$, independently of one another, denoting hydrogen, alkyl radicals having 1 to 12 C atoms or hydroxyl-substituted alkyl radicals having 2 to 3 C atoms. Iminodisuccinic acid (IDS) and (hydroxy)iminodisuccinic acid (HIDS) and alkali metal salts or ammonium salts thereof are especially preferred succinate based builder salts. Especially preferred are the sodium salts thereof.

MGDA, GLDA, IDS and HIDS are especially preferred amino acid based and succinate based builders according to the present invention and mixtures thereof may also be used.

Any suitable form of the amino acid and succinate based compounds in the preceding paragraphs may be used.

Conventional amounts of these phosphorous free builders may be used, typically with an amount in the range of from 20% wt to 80% wt, such as 25 or 30% wt to 60 or 70% wt being used.

According to one aspect of the present invention a mixture of a phosphorous containing builder such as STPP and a non-phosphorous containing builder such as MGDA, GLDA, IDS, HIDS and/or citrates may be used. The weight proportions of each builder can be selected according to the needs of the formulator.

Preferably the total amount of builder present in the composition is at least 10 wt %, and most preferably at least 15 wt %, preferably in an amount of up to 80 wt %, preferably up to 65 wt %, more preferably up to 60 wt %. The actual amount used in the compositions will depend upon the nature of the builder used.

d) Optional Ingredients

The detergent compositions of the invention may also comprise additional optional ingredients in addition to the claimed surfactant. These ingredients may also be present in any other detergent composition used in conjunction with the composition of the invention to form a multi-phase unit dose detergent composition. Where reference is made below to a weight percentage based it is to the weight percentage of the composition comprising that ingredient. For the composition of the invention this is based simply upon the weight of that composition. Where the composition forms part of a multi-phase unit dose detergent composition the amount is stated as based upon the weight of that part of the multi-phase unit dose composition which contains the specified ingredient.

In addition to the particular liquid mixed alkoxylated fatty alcohol surfactants described above which are an essential component of the detergent compositions of the invention, they may also comprise one or more further surfactants. Any other detergent compositions used with the compositions of the invention in the multi-phase unit dose compositions of the invention may also comprise surfactant as described herein.

If any further surfactant is present it may be any of nonionic, anionic, cationic, amphoteric or zwitterionic surface active agents or mixtures thereof although cationic surfactants are less preferred. Many such suitable surfactants are described in Kirk Othmer's Encyclopedia of Chemical Technology, 3rd Ed., Vol. 22, pp. 360-379, "Surfactants and Detersive Systems", incorporated by reference herein.

For automatic dishwashing compositions according to the present invention non-ionic surfactants are especially preferred. For other cleaning applications, such as floors and walls, other surfactants such as anionic surfactants may also be included and suitable types are well known in the art.

The additional nonionic surfactants which may be used include any solid nonionic surfactant and any nonionic surfactants which do not contain more of the lower alkoxylate than of the higher alkoxylate.

Additional nonionic surfactants which may be used (excluding any falling into the essential liquid mixed alkoxylate fatty alcohol non-ionic surfactants class above) include ethoxylated non-ionic surfactants prepared by the reaction of a monohydroxy alkanol or alkylphenol with 6 to 20 carbon atoms which are not liquid or which do not contain more of the lower alkoxylate than of the higher alkoxylate. Preferably the surfactants have at least 12 moles particularly preferred at least 16 moles, and still more preferred at least 20 moles, such as at least 25 moles of ethylene oxide per mole of alcohol or alkylphenol. Particularly preferred non-ionic surfactants suitable for use as the additional nonionic surfactants are those from a linear chain fatty alcohol with 16-20 carbon atoms and at least 12 moles, particularly preferred at least 16 and still more preferred at least 20 moles, of ethylene oxide per mole of alcohol.

The additional fatty alcohol non-ionic surfactants may be prepared as described above for the mixed alkoxylate fatty alcohol nonionic surfactants.

The use of mixtures of different nonionic surfactants is suitable in the context of the present invention for instance mixtures of alkoxylated alcohols and hydroxy group containing alkoxylated alcohols.

Preferably the total amount of non-ionic surfactants is in an amount of from 0.1% wt to 20% wt, more preferably 0.5% wt to 15% wt, such as 1 to 10% wt based on the weight of the composition(s) comprising the surfactant.

An especially preferred optional ingredient in the detergent compositions of the invention is a polymer. Suitable polymers include those comprising polycarboxylic groups such as polyacrylate homopolymers and copolymers and the salts thereof. Copolymers of polycarboxylic acids such as acrylic acids with sulphonated monomers are especially preferred according to the present invention as it has been found that the combination of a sulphonated polymer with the claimed surfactant system provides significant benefits in shine and anti-spotting properties of the detergent composition.

Preferred examples of the sulphonated polymers include copolymers of $CH_2=CR^1-CR^2R^3-O-C_4H_3R^4-SO_3X$ wherein $R^1$, $R^2$, $R^3$, $R^4$ are independently 1 to 6 carbon alkyl or hydrogen, and X is hydrogen or alkali with any suitable other monomer units including modified acrylic, fumaric, maleic, itaconic, aconitic, mesaconic, citraconic and methylenemalonic acid or their salts, maleic anhydride, acrylamide, alkylene, vinylmethyl ether, styrene and any mixtures thereof. Other suitable sulfonated monomers for incorporation in sulfonated (co)polymers are 2-acrylamido-2-methyl-1-propanesulphonic acid, 2-methacrylamido-2-methyl-1-propanesulphonic acid, 3-methacrylamido-2-hydroxy-propanesulphonic acid, allysulphonic acid, methallysulphonic acid, 2-hydroxy-3-(2-propenyloxy)propanesulphonic acid, 2-methyl-2-propenen-1-sulphonic acid, styrenesulphonic acid, vinylsulphonic acid, 3-sulphopropyl acrylate, 3-sulphopropylmethacrylate, sulphomethylacrylamide, sulphomethylmethacrylamide and water soluble salts thereof. Suitable sulphonated polymers are also described in U.S. Pat. No. 5,308,532 and in WO 2005/090541.

It is especially preferred that the sulphonated polymer comprises monomers of a carboxylic acid and a sulphonated monomer, especially acrylic acid and/or 2-acrylamido-2-methyl-1-propanesulphonic acid (AMPS). It is most preferred that the sulphonated polymer is a copolymer of acrylic acid and AMPS, especially in a weight ratio (of the monomers) of 50:50 to 90:10, such as 70:30 to 80:20.

When a sulfonated polymer is present, it is preferably present in the detergent composition of the invention in an amount of at least 0.5 wt %, preferably at least 1 wt %, more preferably at least 2 wt %, and most preferably at least 3 wt %, up to 40 wt %, preferably up to 30 wt %, more preferably up to 20 wt %, and most preferably up to 15 wt %.

In one embodiment of the invention for a multi-phase unit dose composition it is preferred that a sulphonated polymer is present in the detergent composition of the invention and in at least one further detergent composition forming at least one further phase of the multi-phase unit dose composition.

It is also possible to include a polymer which is a polyaspartic acid derivative of formula (I):

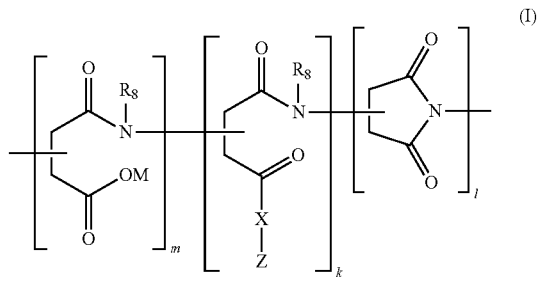

wherein:

M is selected from the group H, alkali metals, ammonium, optionally substituted alkylammonium or a mixture thereof;

X is selected from the group $NR^1$, O and S or a mixture thereof, wherein $R^1$ is H or $C_{1-20}$ hydrocarbyl optionally substituted with hydroxy or $C_{1-8}$ alkyl;

Z is $R^2Y_n$, wherein:
$R^2$ is selected from the group comprising: linear or branched $C_1$-$C_{20}$ alkyl, $C_{5-20}$ aralkyl, each optionally substituted with $C_{1-8}$ alkyl or cyclic $C_{3-10}$ alkyl, wherein the aralkyl may contain one or more heteroatoms selected from N, O and S; and linear and branched —$R^3$—$(R^3O)_p$ or —$R^5$—$(N(R^4)R^5)_q$ wherein $R^3$ and $R^5$ are selected from linear or branched $C_1$-$C_{10}$ alkyl and wherein $R^4$ is selected from the same group as $R^1$ and p and q are integers from 1 to 100;

each Y is independently selected from the group of hydrophilic substituents containing OH; $OR^{10}$; $SO_3M$; $SO_2M$; $SO_3R^{11}$; $SO_2R^{12}$; $OSO_3M$; $OSO_2M$; $OSO_3R^{11}$; $OSO_2R^{12}$; $PO_3M$; $PO_2M$; $PO_3R^{11}$; $PO_2R^{12}$; $OPO_3M$; $OPO_2M$, $OPO_3R^{11}$; $OPO_2R^{12}$; COOM; $COOR^{13}$ wherein $R^{10}$, $R^{11}$, $R^{12}$ and $R^{13}$ are each selected independently from each other from the group defined for $R^6$; and/or the group of hydrophobic substituents containing $NR^{14}R^{15}$ and $NR^{14}R^{15}R^{16}$ wherein $R^{14}$, $R^{15}$ and $R^{16}$ are each independently selected from linear or branched $C_1$-$C_{20}$ alkyl, cyclic $C_{3-10}$ alkyl or $C_{5-20}$ aralkyl, each optionally substituted with $C_{1-8}$ alkyl or cyclic $C_{3-10}$ alkyl, wherein the aralkyl may contain one or more heteroatoms selected from N, O and S;

$R^8$ is H or is selected from the same group as $R^2$;
provided that when X is $NR^1$, then Y is not $SO_3M$, $SO_2M$, $SO_3R^{11}$, $SO_2R^{12}$, $OSO_3M$, $OSO_2M$, $OSO_3R^{11}$ or $OSO_2R^{12}$;
n is an integer from 1 to 20;
k, l are each independently integers from 0 to 860; and
m is an integer from 1 to 860.

According to a further embodiment of the first aspect of the present invention, there is provided a composition comprising a compound of formula (I) as hereinbefore described wherein:

M is selected from the group H, alkali metals, ammonium, optionally substituted alkylammonium or a mixture thereof;
X is selected from the group $NR^1$, O and S or a mixture thereof, wherein $R^1$ is H or $C_{1-20}$ hydrocarbyl optionally substituted with hydroxy or $C_{1-8}$ alkyl;
Z is $R^2Y_n$, wherein
$R^2$ is selected from the group comprising: linear or branched $C_1$-$C_{20}$ alkyl, $C_{5-20}$ aralkyl, each optionally substituted with $C_{1-8}$ alkyl or cyclic $C_{3-10}$ alkyl, wherein the aralkyl may contain one or more heteroatoms selected from N, O and S; and
linear and branched —$R^3$—$(R^3O)_p$ or —$R^5$—$(N(R^4)R^5)_q$ wherein $R^3$ and $R^5$ are selected from linear or branched $C_1$-$C_{10}$ alkyl and wherein $R^4$ is selected from the same group as $R^1$ and p and q are integers from 1 to 100;
each Y is independently selected from the group of hydrophilic substituents containing OH; $OR^{10}$; $SO_3M$; $SO_2M$; $SO_3R^{11}$; $SO_2R^{12}$; $OSO_3M$; $OSO_2M$; $OSO_3R^{11}$; $OSO_2R^{12}$; $PO_3M$; $PO_2M$; $PO_3R^{11}$; $PO_2R^{12}$; $OPO_3M$; $OPO_2M$, $OPO_3R^{11}$; $OPO_2R^{12}$; COOM; $COOR^{13}$ wherein $R^{10}$, $R^{11}$, $R^{12}$ and $R^{13}$ are each selected independently from each other from the group defined for $R^6$; and/or the group of hydrophobic substituents containing H, $NR^{14}R^{15}$ and $NR^{14}R^{15}R^{16}$ wherein $R^{14}$, $R^{15}$ and $R^{16}$ are each independently selected from linear or branched $C_1$-$C_{20}$ alkyl, cyclic $C_{3-10}$ alkyl or $C_{5-20}$ aralkyl, each optionally substituted with $C_{1-8}$ alkyl or cyclic $C_{3-10}$ alkyl, wherein the aralkyl may contain one or more heteroatoms selected from N, O and S;
$R_8$ is H or is selected from the same group as $R^2$;
provided that the molar ratio of hydrophobic:hydrophilic substituents is from 1:1.1 to 1:1000.
n is an integer from 1 to 20;
k, l are each independently integers from 0 to 860; and
m is an integer from 1 to 860.

The polyaspartic acid derivatives may be included in the compositions of the invention in amounts 0.1-40% wt, such as 5-30% wt.

The compositions of the invention may also comprise one or more thickeners to control the viscosity thereof. Any suitable thickeners as known in the art may be used with gums, polymers and gels being preferred. For example, polyethylene glycols, e.g. PEG with a molecular weight in the range of 5000 to 15,000 may be used as a thickener. Thickeners are typically present in amounts of up to 2% wt.

The detergent composition of the invention may also comprise one or more foam control agents and indeed this is preferred. Suitable foam control agents for this purpose are all those conventionally used in this field, such as, for example, silicones and their derivatives and paraffin oil. The foam control agents are preferably present in the composition in amounts of 0.5% by weight or less of the total weight of the composition.

The detergent compositions of the invention may also comprise minor, conventional, amounts of preservatives, dyes, colurants and perfume as desired. Such ingredients are typically present in amounts of up to 2% wt.

Solvents may also be included in the liquid detergent compositions of the invention, for example glycols such as 1,2 propylene glycol. Typically solvents, if used are present in amounts of up to 10% wt, preferably in amounts of up to 5% wt.

The detergent compositions of invention may comprise bleaching compounds although generally they will be substantially free of bleaching compounds. The detergent composition of the invention may also be used as part of a multi-phase unit dose detergent composition. In this case the other detergent compositions making up the multi-phase unit dose detergent composition may comprise a bleaching compound and preferably they do so.

Any conventional bleaching compound can be used in any conventional amount in either the composition of the invention or in any other detergent composition forming part of the multi-phase unit dose detergent composition.

When a bleach is present, it is preferably present in the relevant composition in an amount of at least 1 wt %, more preferably at least 2 wt %, more preferably at least 4 wt %. Preferably it is present in the relevant composition in an amount of up to 30 wt %, more preferably up to 20 wt %, and most preferably up to 15 wt %. Amounts of 1% to 30% wt of bleach component are especially preferred.

Most preferably the bleach is selected from inorganic peroxy-compounds and organic peracids and the salts derived therefrom.

Examples of inorganic perhydrates include persulfates such as peroxymonopersulfate (KMPS), perborates or percarbonates. The inorganic perhydrates are normally alkali metal salts, such as lithium, sodium or potassium salts, in particular sodium salts. The inorganic perhydrates may be present in the detergent as crystalline solids without further protection. For certain perhydrates, it is however advantageous to use them as granular compositions provided with a coating which gives the granular products a longer shelf life.

The preferred percarbonate is sodium percarbonate of the formula $2Na_2CO_3 \cdot 3H_2O_2$. A percarbonate, when present, is preferably used in a coated form to increase its stability.

Organic peracids include all organic peracids traditionally used as bleaches, including, for example, perbenzoic acid and peroxycarboxylic acids such as mono- or diperoxyphthalic acid, 2-octyldiperoxysuccinic acid, diperoxydodecanedicarboxylic acid, diperoxy-azelaic acid and imidoperoxycarboxylic acid and, optionally, the salts thereof. Especially preferred is phthalimidoperhexanoic acid (PAP).

When a composition of the invention, or a unit dose composition comprising a composition of the invention, comprises a bleach it may also comprise one or more bleach activators or bleach catalysts depending upon the nature of the bleaching compound. Any suitable bleach activator may be included for example TAED. Any suitable bleach catalyst may be used for example manganese acetate or dinuclear manganese complexes such as those described in EP-A-1, 741,774. Conventional amounts may be used e.g. in amounts of from 1 to 30 t %, more preferred of from 5 to 25 wt % and most preferred of from 10 to 20 wt % based on the weight of the part of the composition comprising the bleach.

The detergent compositions of the invention, or other detergent compositions included in the multi-phase unit dose compositions, may comprise one or more anti-corrosion agents especially when the detergent compositions are for use in automatic dishwashing operations. These anti-corrosion agents may provide benefits against corrosion of glass and/or metal and the term encompasses agents that are intended to prevent or reduce the tarnishing of non-ferrous metals, in particular of silver and copper. It may be desirable to include more than one type of anti-corrosion agent to provide protection against corrosion of glass and metals.

Organophosphoric acids are often used as corrosion inhibitors. Diphosphoric acids and their salts are preferred according to the present invention with the tetrasodium and disodium salts being especially preferred. 1, hydroxy, ethylidene 1,1-diphosphoric acid (HEDP) and it tetrasodium or disodium salts is especially preferred. The organophosphoric acid is preferably used in an amount of from 0.05 to 10% wt, such as 0.1 to 7.5% wt based on the weight of the composition in which it is present.

It is known to include a source of multivalent ions in detergent compositions, and in particular in automatic dishwashing compositions, for anti-corrosion benefits. For example, multivalent ions and especially zinc, bismuth and/or manganese ions have been included for their ability to inhibit such corrosion. Organic and inorganic redox-active substances which are known as suitable for use as silver/copper corrosion inhibitors are mentioned in WO 94/26860 and WO 94/26859. Suitable inorganic redox-active substances are, for example, metal salts and/or metal complexes chosen from the group consisting of zinc, bismuth, manganese, titanium, zirconium, hafnium, vanadium, cobalt and cerium salts and/or complexes, the metals being in one of the oxidation states II, III, IV, V or VI. Particularly suitable metal salts and/or metal complexes are chosen from the group consisting of $MnSO_4$, Mn(II) citrate, Mn(II) stearate, Mn(II) acetylacetonate, Mn(II) [1-hydroxyethane-1,1-diphosphonate], $V_2O_5$, $V_2O_4$, $VO_2$, $TiOSO_4$, $K_2TiF_6$, $K_2ZrF_6$, $CoSO_4$, $Co(NO_3)_2$ and $Ce(NO_3)_3$. Any suitable source of multivalent ions may be used, with the source preferably being chosen from sulphates, carbonates, acetates, gluconates and metal-protein compounds. Zinc salts are specially preferred corrosion inhibitors.

Preferred silver/copper anti-corrosion agents are benzotriazole (BTA) or bis-benzotriazole and substituted derivatives thereof. Other suitable agents are organic and/or inorganic redox-active substances and paraffin oil. Benzotriazole derivatives are those compounds in which the available substitution sites on the aromatic ring are partially or completely substituted. Suitable substituents are linear or branch-chain $C_{1-20}$ alkyl groups and hydroxyl, thio, phenyl or halogen such as fluorine, chlorine, bromine and iodine. A preferred substituted benzotriazole is tolyltriazole (TTA).

Therefore, an especially preferred optional ingredient according to the present invention is a source of multivalent ions such as those mentioned in the immediately preceding paragraphs and in particular compounds comprising zinc, bismuth and/or manganese ions and/or benzotriazole, including substituted benzotriazoles. In particular a source of zinc ions and unsubstituted benzotriazole are preferred as anti-corrosion agents and a mixture of these two ingredients is especially preferred according to the invention.

Any conventional amount of the anti-corrosion agents may be included in the solid detergent compositions of the invention. However, it is preferred that they are present in an total amount of from 0.01% wt to 5% wt, preferably 0.05% wt to 3% wt; more preferably 0.1 to 2.5% wt, such as 0.2% wt to 2% wt based on the total weight of the composition. If more than one anti-corrosion agent is used, the individual amounts may be within the preceding amounts given but the preferred total amounts still apply.

The compositions of the invention may optionally comprise one or more enzymes. Any type of enzyme typically used in detergent compositions may be included in the compositions of the present invention. It is preferred that the enzyme(s) is/are selected from proteases, lipases, amylases, cellulases laccases, catalases and peroxidases. It is most preferred that protease and/or amylase enzymes are included in the compositions according to the invention as such enzymes are especially effective in dishwashing detergent compositions. Any suitable species of these enzymes may be used as desired. Conventional amounts of such enzymes may be used.

The compositions according to the invention, and/or any detergent composition used therewith in a multi-phase unit dose composition, may also comprise a source of acidity or a source of alkalinity (to obtain the desired pH on dissolution) especially if the composition is to be used in an automatic dishwashing application.

A source of alkalinity may suitably be any suitable basic compound for example any salt of a strong base and a weak acid. When an alkaline composition is desired silicates are amongst the suitable sources of alkalinity. Preferred silicates are sodium silicates such as sodium disilicate, sodium metasilicate and crystalline phyllosilicates. Other suitable sources of alkalinity may be a carbonate or bicarbonate (such as the alkali metal or alkaline earth metal salts with sodium carbonate being especially preferred). A source of acidity may suitably be any suitable acidic compound for example a polycarboxylic acid. Conventional amounts of the alkalinity or acidity source may be used.

The detergent compositions can be prepared by any suitable method. However, it has been found that they exhibit especially good stability if they are produced by mixing the ingredients together at a temperature in the range of from 25-50° C., preferably of from 30-40° C. This has been found to result in liquid compositions which typically show good stability for at least three months at room temperature.

The present invention also provides a method of improving shine and/or inhibiting spotting on hard surfaces such as kitchenware and especially glassware. In particular the method is carried out by treating kitchenware items in an automatic dishwasher by the step of contacting a detergent composition according to either the first or second aspect of the invention with kitchenware items during a dishwashing cycle. Suitable conditions to effect the removal are employed in the method and will typically involve contact under aqueous conditions and usually at a temperature in the range of from 15-70° C., such as 30-70° C.

According to third aspect of the invention it is preferred that the detergent composition of the invention forms a part of an overall dishwashing composition such as a multi-phase unit dose composition. A unit dose detergent composition is designed to be used as a single portion of detergent composition in a single washing operation. Of course, one or more of such single portions may be used in a cleaning operation if desired. The additional detergent may be of any physical form e.g. liquid, powder, granules, shaped body etc.

One type of preferred unit dose composition according to the present invention comprises the detergent composition of the invention at least partially enveloped by a water soluble or water dispersible package. Thus this is a unit dose detergent composition intended to be consumed in a single washing operation. It is preferred that the water soluble or water dispersible packaging material fully envelopes the detergent composition. In this aspect the detergent composition of the invention may be present within the water soluble or dispersible package either on its own (e.g. as a gel encased in a water soluble single compartment package) or it may form a part of a water soluble package containing two or more different detergent compositions. In this latter arrangement it is preferred that the water soluble package is a multi-compartment package with each compartment containing one or more detergent compositions.

It is preferred according to one embodiment of the invention that the water soluble or water dispersible package comprises a plurality of compartments, typically 2 to 5 compartments. This has the advantage of allowing incompatible ingredients of the overall formulation to be physically separated from each other which can increase the stability of the overall composition.

The water soluble or water dispersible package comprising the detergent of the invention may be of any suitable form e.g. flexible pouch or a self-supporting body such as one with a substantially planar base and upstanding side walls which container is typically closed with a film lid. In some embodiments of the invention it may comprise a partially pre-formed container. Preferred examples of such containers include gelatin capsules, such as those employed in medicament applications. When gelatin is used it will be appreciated that the formulation and the physical nature of the gelatin may wary widely. For example the gelatin may be a hard gelatin or a soft gelatin (having a plasticiser component such as water, glycerine, mono-propylene glycol or polyethylene glycol).

As stated above the water soluble or water dispersible package may be in the form of a self supporting body. Preferably this is a self-supporting body with a substantially planar base and upstanding side walls which is typically closed with a film lid. Such a body may be of any shape but will typically be of a substantially square or rectangular cross section. The package may also not be in the form of a walled container but instead a shape, which is substantially self supporting (optionally with pores/apertures). The self supporting body preferably comprises a matrix. The matrix may be formed of the material used for the film of the package or alternatively the matrix may comprise a second material. Preferred matrix forming materials include gelatin, especially in an admixture with glycerine, optionally with water. A further preferred matrix forming material is polyethylene glycol (PEG) having a molecular mass of 3000 or above, e.g. such as 6000, 8000, 20000, 35000 or 8 million.

Generally the package has a maximum dimension in at least one plane of between 5 and 60 mm, preferably between 10 and 50 mm, such as between 20 and 45 mm. It will be appreciated that the size of the package will vary in accordance with desires of the unit dose detergent product formulator and the intended use of the package. It is especially preferred that the package has this dimension in at least two planes and most preferably in three planes.

The package may be formed by any suitable method, for example the method described in WO 2004/081161 which method is incorporated by reference herein. If the package is a self supporting body produced by injection moulding then it can be made according to the process disclosed in EP-A-1232100 which is incorporated by reference herein.

When the package comprising the detergent composition is a flexible pouch, the method may comprise the step of enveloping the detergent composition with at least one sheet of the material used to form the packaging, especially a flexible sheet of the packaging material.

One way of producing the water soluble or water dispersible package in the form of a pouch containing the detergent composition of the invention is to form a cavity in a first sheet of the packaging material used to form the pouch and add the detergent composition thereto prior to the packaging material being sealed to produce the water soluble or water dispersible packaging pouch. The package may be sealed by the addition of a second sheet of the packaging material over the cavity containing the detergent composition and sealing it to the first sheet of the packaging material. The first and second sheets of the packaging material may comprise the same or different water soluble or dispersible packaging material however the two sheets preferably comprise the same packaging material.

The water soluble or water dispersible package may be formed by any suitable conventional method, for example, vacuum forming, thermoforming or injection moulding depending upon the type of packaging to be produced e.g. flexible pouch or self supporting container. For example, in a thermoforming process the film may be drawn down or blown down into a mould. Thus, for example, the film is heated to the thermoforming temperature using a thermoforming heater plate assembly, and then drawn down under vacuum or blown down under pressure into the mould.

Plug-assisted thermoforming and pre-stretching the film, for example by blowing the film away from the mould before thermoforming, may, if desired, be used. One skilled in the art can choose an appropriate temperature, pressure or vacuum and dwell time to achieve an appropriate package. The amount of vacuum or pressure and the thermoforming temperature used depend on the thickness and porosity of the film and on the polymer or mixture of polymers being used. Thermoforming of PVOH films is known and described in, for example, WO 00/55045.

Polyvinyl alcohol is one suitable material from which to form the water dispersible or water soluble package (see further details below). A suitable forming temperature for PVOH or ethoxylated PVOH is, for example, from 90 to 130° C., especially 90 to 120° C. A suitable forming pressure is, for example, 69 to 138 kPa (10 to 20 p.s.i.), especially 83 to 117 kPa (12 to 17 p.s.i.). A suitable forming vacuum is 0 to 4 kPa (0 to 40 mbar), especially 0 to 2 kPa (0 to 20 mbar). A suitable dwell time is, for example, 0.4 to 2.5 seconds, especially 2 to 2.5 seconds.

The packaging material used to produce the water soluble or water dispersible package is preferably polymeric and is preferably selected from polyvinyl alcohol, celluloses (including cellulose derivatives), starches, gelatine, polyglycolides, gelatine and polylactides copolymers or a mixture or co-polymer thereof. Polyvinyl alcohol is especially preferred as the packaging material. Preferred cellulose derivatives include hydroxypropyl cellulose ether (HMPC). The polymeric material may be a photopolymer or a co-polymer of any suitable monomers such as those of the aforementioned types.

The water soluble or water dispersible polymeric material may, for example, be formed of a film. The film may be a single film, or a laminated film as disclosed in GB-A-2,244,258. While a single film may have pinholes, the two or more layers in a laminate are unlikely to have pinholes which coincide.

The thickness of at least one, and preferably all, of the external walls of the water soluble or water dispersible package may be up to 2 mm, more preferably up to 1 mm, more preferably 10 to 300 μm, more preferably 20 to 200 μm, especially 25 to 160 μm, more especially 30 to 150 μm and most especially 30 to 150 μm.

The packaging material, e.g. film, may be produced by any process, for example by extrusion and blowing or by casting. The film may be unoriented, monoaxially oriented or biaxially oriented. If the layers in the film are oriented, they usually have the same orientation, although their planes of orientation may be different if desired. The layers in a laminate may be the same or different. Thus they may each comprise the same polymer or a different polymer.

Examples of the water-soluble or dispersible polymeric material which may be used in a single layer film or in one or more layers of a laminate or which may be used for injection moulding or blow moulding are poly(vinyl alcohol) (PVOH), cellulose derivatives such as hydroxypropyl methyl cellulose (HPMC) and gelatin. An example of a suitable PVOH is ethoxylated PVOH. The PVOH may be partially or fully alcoholised or hydrolysed. For example it may be from 40 to 100%, preferably from 70 to 92%, more preferably about 88% or about 92%, alcoholised or hydrolysed. The degree of hydrolysis is known to influence the temperature at which the PVOH starts to dissolve in water. 88% hydrolysis corresponds to a film soluble in cold (i.e. room temperature) water, whereas 92% hydrolysis corresponds to a film soluble in warm water. Therefore the water soluble characteristics of the film can be controlled.

The invention is further described with reference to the following non-limiting Examples. Further examples within the scope of the invention will be apparent to the person skilled in the art.

EXAMPLES

Example 1

Two multi-phase unit dose automatic dishwashing compositions having the formulations as shown below in Table 1 were prepared as described below. The compositions comprise a gel according to the invention and also two additional powder compositions herein designated as powder 1 and powder 2. The gel composition and the two powder compositions are placed into separate compartments of a water soluble injection moulded pre-formed polyvinyl-alcohol container having three compartments to form the multi-phase unit dose composition. All percentages are given as % wt based on the total weight of the composition.

Formulation 1 is a comparative example comprising gel detergent composition an ethoxylated fatty alcohol non-ionic surfactant which is not according to the present invention comprises a gel detergent composition according to the invention. Formulation 2 comprises a gel detergent composition according to the invention.

Powder 1 is formed by mixing together the given amounts of sodium carbonate, sodium percarbonate and sodium tripolyphosphate.

Powder 2 is formed by mixing together the given amounts of TAED, Protease granules, Amylase granules, Manganese acetate and the sulfonated copolymer.

The gel composition is formed by mixing the liquid non-ionic surfactant, the two thickeners (PEG 6000 and the EO/PO thickener) with the sodium tripolyphosphate (for use in gel) in an Ystral X50/10 mixer at room temperature for 20 minutes at a speed or 1000 revolutions per minute until it yielded a fine dispersion of solids and liquids which formed a gel. This dispersion did not show any appreciable phase separation after three months storage at room temperature.

TABLE 1

| | Formulation 1 | |
|---|---|---|
| Component in wt % | Formulation 1 (comparative) | Formulation 2 |
| Powder 1 | | |
| Sodium carbonate | 8.0 | 8.0 |
| Sodium percarbonate | 15.0 | 15.0 |
| Sodium Tripolyphosphate (STPP) | 45.0 | 45.0 |
| Powder 2 | | |
| TAED | 5.0 | 5.0 |
| Protease granules | 1.0 | 1.0 |
| Amylase granules | 0.5 | 0.5 |
| Managanese acetate | 0.5 | 0.5 |
| Sulfonated co-polymer*[1] | 8.0 | 8.0 |
| Gel composition of the invention | | |
| Liquid nonionic surfactant ($C_{11}$-$EO_5$-$PO_5$), | 5.0 | 0.0 |
| Liquid nonionic surfactant ($C_{12}$-$C_{15}$-$EO_8$-$PO_4$), | 0.0 | 5.0 |
| Sodium Tripolyphosphate (STPP) for gel | 10.0 | 10.0 |
| PEG 6000 as thickener | 1.5 | 1.5 |
| Statistical EO-PO thickener with mole ratio 4:1 and Mw 12000 g/mol. | 0.5 | 0.5 |
| Total % wt | 100.0 | 100.0 |
| pH measured 1 wt % in water at 20° C. | 9.8 | 9.8 |

*[1] Available ex Rohm and Haas, a copolymer of Acrylic acid and AMPS in a wt ratio of 74:26.

For both formulations, 8.5 g of Powder 1 was placed into a first compartment of the polyvinyl alcohol water soluble capsule. 4.5 g of Powder 2 was placed into a second compartment of the polyvinyl alcohol water soluble capsule. 3.0 g of the gel composition of the invention was placed into a third compartment of the polyvinyl alcohol water soluble capsule. The water soluble filled capsule was then sealed with a Polyvinyl alcohol water soluble film (Monosol PT 75). The capsule weight was 2.5 g. Thus the total filled capsule weight was 18.5 g.

Example 2

Formulation 1 and Formulation 2 were tested for their shine profile/anti-spotting properties in a Bosch SGS058M02EU/36 dishwashing machine using the Eco 50° C.+Vario Speed (no 3-in-1 function) program following the Rinse Performance method as described below.

A capsule according to Formulation 1 or Formulation 2 was added into the dosing chamber of the dishwasher and the machine was run on the above dishwashing program.

The dishwasher was loaded with glassware (long drink glasses) as described below. The water hardness was 21° GH. This test is repeated 5 times for each formulation.

Spotting/filming on the long drink glassware after 5 dishwashing cycles was assessed by viewing the glasses in a lit black box. The results are given in Table 2 and are expressed on a scale of 1 to 10 (1 being worst with extreme spotting and filming and 10 being best with no visible spotting and filming).

TABLE 2

| Rinse Performance | | |
| --- | --- | --- |
| | Formulation 1 (comparative) | Formulation 2 |
| Spotting | 3.0 | 6.0 |
| Filming | 7.0 | 7.0 |

The rinse performance results above demonstrate that the compositions of the invention exhibit better anti-spotting properties that the comparative example. This also results in a better perception of shine on the glasses by the consumer.

The invention claimed is:

1. A method of automatic dishwashing, wherein the method comprises the steps of:
   carrying out at least one main washing cycle and at least one rinse cycle in an automatic dishwashing machine; and
   providing a composition to the automatic dishwashing machine during the at least one main washing cycle;
   wherein the composition is a liquid automatic dishwashing detergent composition comprising:
   a liquid mixed alkoxylate fatty alcohol non-ionic surfactant comprising at least one lower alkoxylate group and at least one higher alkoxylate group, wherein there is a greater number of moles of the lower alkoxylate group than of the higher alkoxylate group in the molecule, wherein the liquid mixed alkoxylate fatty alcohol non-ionic surfactant has the formula:

$R1-[EO]n-[PO]m-[BO]p-Bu q$ wherein:
   R1 is an alkyl group of between C8 and C20;
   EO is ethylene oxide;
   PO is propylene oxide;
   BO is butylene oxide;
   Bu is butylene;
   n is an integer from 6 to 10;
   m is an integer from 3 to 5;
   p is 0;
   q is 0; and
   a builder.

2. The method according to claim 1, wherein the liquid automatic dishwashing detergent composition is a gel.

3. The method according to claim 1, wherein the liquid mixed alkoxylate fatty alcohol non-ionic surfactant comprises 4 moles of PO and 8 moles of EO in the molecule.

4. The method according to claim 1, wherein the liquid automatic dishwashing detergent composition comprises 2 to 30% wt of the liquid mixed alkoxylate fatty alcohol non-ionic surfactant.

5. The method according to claim 1, wherein the builder is selected from phosphate-containing builders, polycarboxylic acids and their salts and amino acid based builders.

6. The method according to claim 5, wherein the builder is selected from tripolyphosphates, citrates, MGDA and GLDA and salts or derivatives and mixtures thereof.

7. The method according to claim 1, wherein the liquid automatic dishwashing detergent composition further comprises a polymer.

8. The method according to claim 7, wherein the polymer is a sulphonated polymer.

9. The method according to claim 8, wherein the sulphonated polymer comprises monomers of a carboxylic acid or a salt thereof and a sulphonated monomer.

10. The method according to claim 1, wherein the liquid automatic dishwashing detergent composition further comprises additional non-ionic surfactant.

11. The method according to claim 1, wherein the liquid automatic dishwashing detergent composition is prepared at a temperature in the range of from 25-80° C.

12. The method according to claim 11, wherein the liquid automatic dishwashing detergent composition is prepared at a temperature in the range of from 30-50° C.

13. The method according to claim 1, wherein the liquid automatic dishwashing detergent composition is in the form of a unit dose and is enveloped in a water soluble or water dispersible package.

14. The method according to claim 13, wherein the water soluble or water dispersible package has a plurality of compartments.

15. The method according to claim 13, wherein the water soluble or water dispersible package comprises polymeric packaging material.

16. The method according to claim 15, wherein the polymeric packaging material is selected from polyvinyl alcohol, celluloses and cellulose derivatives, starches, gelatine, polyglycolides, gelatine and polylactides copolymers or a mixture or co-polymer thereof.

17. The method according to claim 1, wherein the liquid mixed alkoxylate fatty alcohol non-ionic surfactant is derived from a linear chain fatty alcohol having 12-15 carbon atoms.

18. The method according to claim 1, wherein the liquid mixed alkoxylate fatty alcohol non-ionic surfactant has at least 10 moles of alkylene oxide per mole of alcohol.

19. The method according to claim 1, wherein the liquid automatic dishwashing detergent composition comprises at least 2 wt % of the liquid mixed alkoxylate fatty alcohol non-ionic surfactant.

20. The method according to claim 1, wherein the liquid automatic dishwashing detergent composition comprises at least 10 wt % of the builder.

21. The method according to claim 1, wherein any solvent included in the liquid automatic dishwashing detergent composition is present in an amount of no more than 10 wt %.

22. The method according to claim 1, wherein the liquid mixed alkoxylate fatty alcohol non-ionic surfactant comprises 4 or 5 moles of PO and 7 or 8 moles of EO.

23. The method according to claim 1, wherein the liquid mixed alkoxylate fatty alcohol non-ionic surfactant is derived from a linear chain fatty alcohol having 12-18 carbon atoms.

* * * * *